United States Patent
Pees et al.

(10) Patent No.: US 8,431,728 B2
(45) Date of Patent: Apr. 30, 2013

(54) PROCESS FOR THE AMMONOLYSIS OF 11-BROMOUNDECANOIC ACID

(75) Inventors: Bernard Pees, Brionne (FR); Stephanie Lebrun, Nassandres (FR)

(73) Assignee: Arkema France, Colombes (FR)

( * ) Notice: Subject to any disclaimer, the term of this patent is extended or adjusted under 35 U.S.C. 154(b) by 194 days.

(21) Appl. No.: 13/140,547

(22) PCT Filed: Dec. 15, 2009

(86) PCT No.: PCT/FR2009/052536
§ 371 (c)(1),
(2), (4) Date: Jun. 17, 2011

(87) PCT Pub. No.: WO2010/070228
PCT Pub. Date: Jun. 24, 2010

(65) Prior Publication Data
US 2011/0251414 A1    Oct. 13, 2011

(30) Foreign Application Priority Data
Dec. 19, 2008  (FR) ...................................... 08 07259

(51) Int. Cl.
*C07C 227/00*  (2006.01)
(52) U.S. Cl.
USPC ....................................................... 554/114

(58) Field of Classification Search .................... 554/114
See application file for complete search history.

(56) References Cited

FOREIGN PATENT DOCUMENTS
GB           591027      8/1947
GB           591027 A1 *  8/1947

OTHER PUBLICATIONS

Gudadhe, S., et al., "Kinetic studies of animation of 11-bromoundecanoic acid", Industrial & Engineering Chemistry Process Design and Development, (1986), 354-357.

* cited by examiner

*Primary Examiner* — Deborah D Carr
(74) *Attorney, Agent, or Firm* — Smith, Gambrell & Russell, LLP

(57) ABSTRACT

The invention relates to a process for the ammonolysis of 11-aminoundecanoic acid, carried out under conditions that make it possible to limit secondary reactions that produce impurities, especially secondary amine type reactions, while considerably reducing the reaction time. According to the invention, the process comprises the following steps: i) a step of dispersing 11-bromoundecanoic acid, molten or non-molten, in an aqueous solution of ammonia, and ii) an ammonolysis step comprising the reaction of 11-bromoundecanoic acid with excess ammonia water under conditions whereby the reaction medium is stirred and heated gradually so as to obtain 11-aminoundecanoc acid with total consumption of the 11-bromoundecanoic acid.

20 Claims, 5 Drawing Sheets

PROCESS FOR THE AMMONOLYSIS OF 11-BROMOUNDECANOIC ACID

Figure 1:
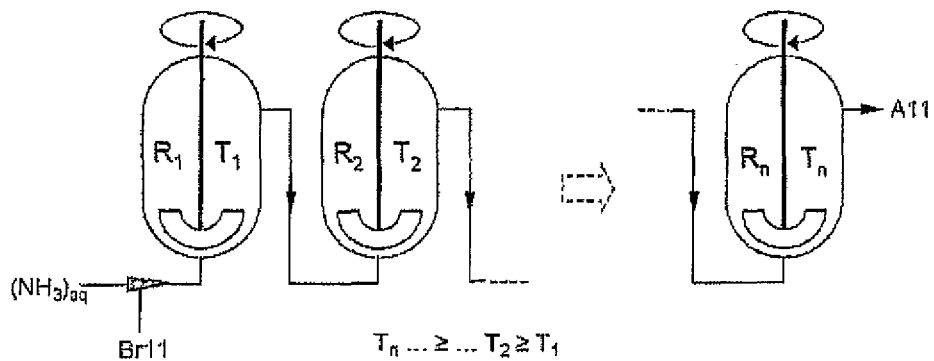

The present invention relates to a process for ammonolysis of 11-bromoundecanoic acid, carried out under conditions which make it possible to limit the side reactions which are the source of the impurities, in particular of secondary amine type, and while reducing the reaction time.

A halogenated acid, 11-aminoundecanoic acid, can be isolated from castor oil, in particular via a reaction earned out in the presence of ammonia, known as ammonolysis. The 11-aminoundecanoic acid thus obtained is used in particular as monomer in the synthesis, by condensation, of homopolymeric polyamides, such as Rilsan® or PA11. Rilsan® PA 11 is the only polymer to provide top of the range performances in different major physical fields, including chemical resistance, resistance to hydrocarbons, impact strength, bursting strength, abrasion resistance, crack resistance, flexibility, a high working temperature and long-term aging. The properties of these polymers are modified when the level of impurities present in the reaction medium during the condensation exceeds a certain threshold. It is therefore desirable to limit as much as possible the formation of by-products.

It is known to react a halogenated acid with an ammonia solution in order to obtain the corresponding aminocarboxylic acid, according to the Hoffmann method for the preparation of amines. The document FR 988 699 describes a process for the preparation of aminocarboxylic acids by subjecting a halogenated acid to the action of aqueous, alcoholic or aqueous/alcoholic ammonia solutions. The reaction takes place at relatively low temperatures. Its rate increases with the temperature. On the other hand, the yield of amino acids decreases with the rise in the temperature. The implementational example cited in this document describes a process for the preparation of 10-aminodecanoic acid which consists in introducing 10-bromodecanoic acid in the molten state into an aqueous ammonia solution comprising 25% by weight of ammonia, in stirring the mixture and in maintaining it at approximately 15° C. The reaction is complete after approximately 6 days and exhibits a yield of 77%.

A rise in the reaction temperature furthermore results in a not insignificant increase in the amount of impurities formed, which is harmful to the properties of the polyamide synthesized from this stream. Subjecting this stream to subsequent treatments for purification and separation of the amino acid results in a not insignificant increase in the cost of manufacture of the polyamides.

Gudadhe et al. (*Ind. Eng. Chem. Process Des. Dev.*, 1986, 25, 354-357) have studied the kinetics of the amination reaction of 11-bromoundecanoic acid. The results appearing in table I of this document show that an increase in the reaction temperature from 30 to 50° C. results in an increase in the reaction rate, accompanied by a decrease in the yield of 11-aminoundecanoic acid. This would be due to the increase in the amount of impurities formed in parallel.

During the reaction for the ammonolysis of 11-bromoundecanoic acid, it is possible to very greatly limit the parallel reactions which are the source of the main impurities (11-hydroxyundecanoic acid HO—$(CH_2)_{10}$—COOH and aminodiundecanoic acid $NH[(CH_2)_{10}$—$COOH]_2$) by reducing the concentration of 11-bromoundecanoic acid and 11-aminoundecanoic acid in the medium. For this, the ammonolysis reaction is carried out in an aqueous and heterogeneous medium. On doing this, the 11-bromoundecanoic acid dissolves in the aqueous phase in the form of the ammonium salt, the solubility at low temperature (lower than 30° C.) of which is very low. It is possible to advantageously restrict the reaction for the aminolysis of 11-bromoundecanoic acid with 11-aminoundecanoic acid, resulting in aminodiundecanoic acid, by using a very large excess of aqueous ammonia. The very high proportion of aqueous ammonia in the medium, in comparison with the 11-aminoundecanoic acid, greatly reduces the probability of encounter between the latter and the 11-bromoundecanoic acid, very significantly limiting their mutual reactivities.

However, carrying out the reaction at low temperature, while it makes it possible to reduce the side reactions and to selectively obtain the 11-aminoundecanoic acid, also results in extremely lengthy reaction times (with complete consumption of the 11-bromoundecanoic acid), which times are incompatible with the use of this reaction on the industrial scale (95 h for an isothermal reaction at 22° C.).

The present invention intends to overcome the disadvantages presented by the known processes for the ammonolysis of 11-bromoundecanoic acid.

The object of the present invention is to provide a process for the ammonolysis of 11-bromoundecanoic acid which makes it possible to obtain 11-aminoundecanoic acid with a highly limited production of by-products and for a shorter reaction time compatible with carrying out the reaction industrially.

It has now been found that only the starting temperature of the reaction for the ammonolysis of 11-bromoundecanoic acid governs the formation of the by-products. It thus necessary not to carry out the reaction according to a low-temperature isotherm but to subject the medium to a regular rise in temperature while observing a starting low-temperature stationary phase (ideally 15 to 25° C.).

A subject-matter of the invention is a process for the manufacture of 11-aminoundecanoic acid from 11-bromoundecanoic acid, comprision of following stages:
i) a stage of dispersion of molten or non-molten 11-bromoundecanoic acid in an aqueous ammonia solution, and
ii) a stage of ammonolysis by reaction of 11-bromoundecanoic acid with excess aqueous ammonia under conditions of stirring the reaction medium and of gradual heating of the latter which are sufficient to make it possible to obtain 11-aminoundecanoic acid with complete consumption of the 11-bromoundecanoic acid in less than 80 h while limiting the formation of aminodiundecanoic acid.

The process forming the subject matter of the present invention, with a reaction carried out at an increasing and non-isothermal temperature, exhibits the advantage of achieving a very high conversion to 11-aminoundecanoic acid while limiting the amount of impurities formed (mainly aminodiundecanoic acid, the level of which in the crude reaction product is less than 3500 ppm, preferably less than 2500 ppm) and while considerably reducing the reaction time.

Figure 3:
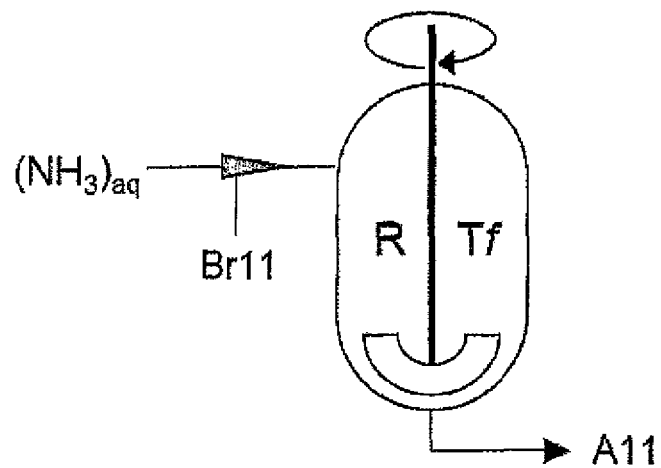
Figure 2:
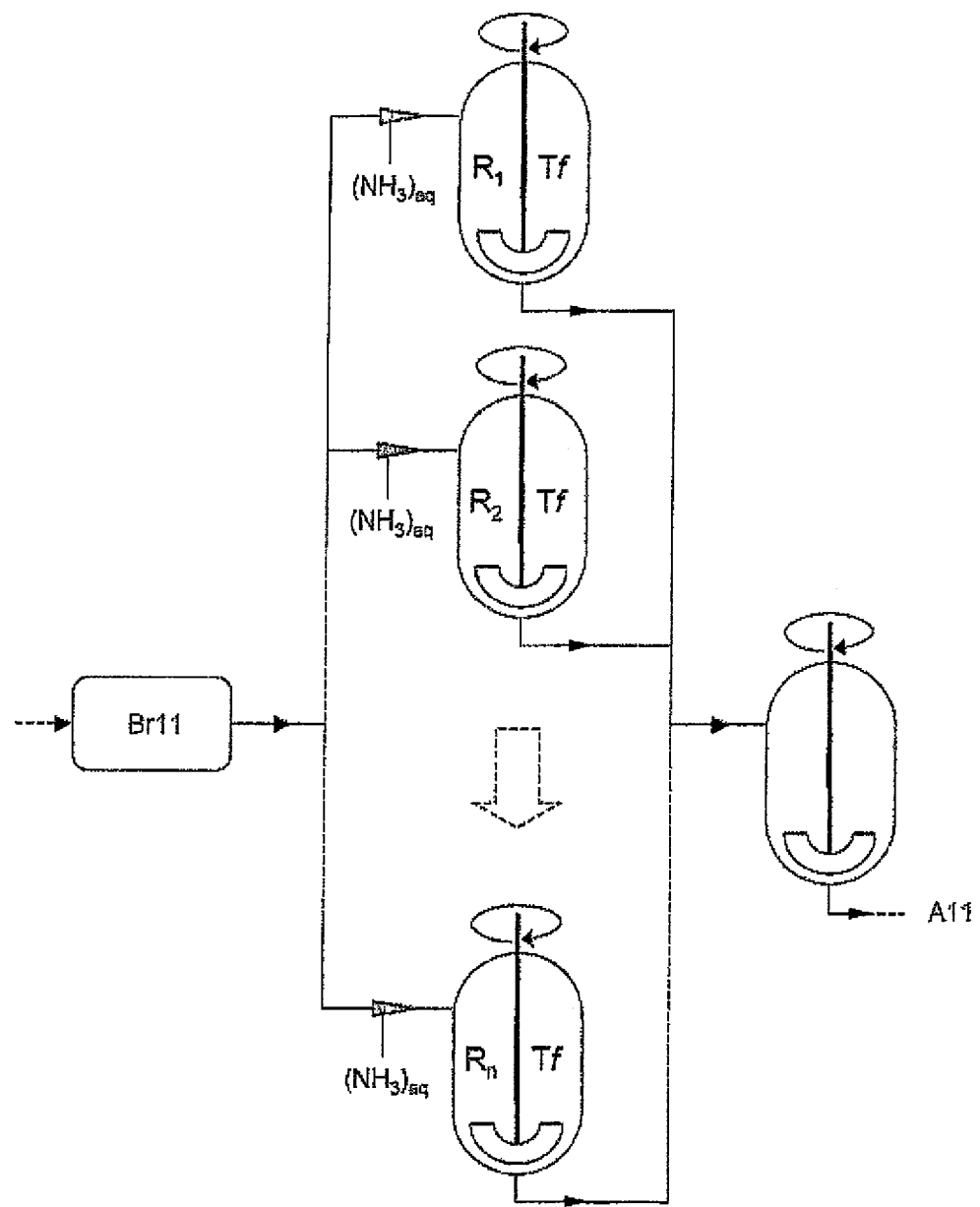
Figure 4:
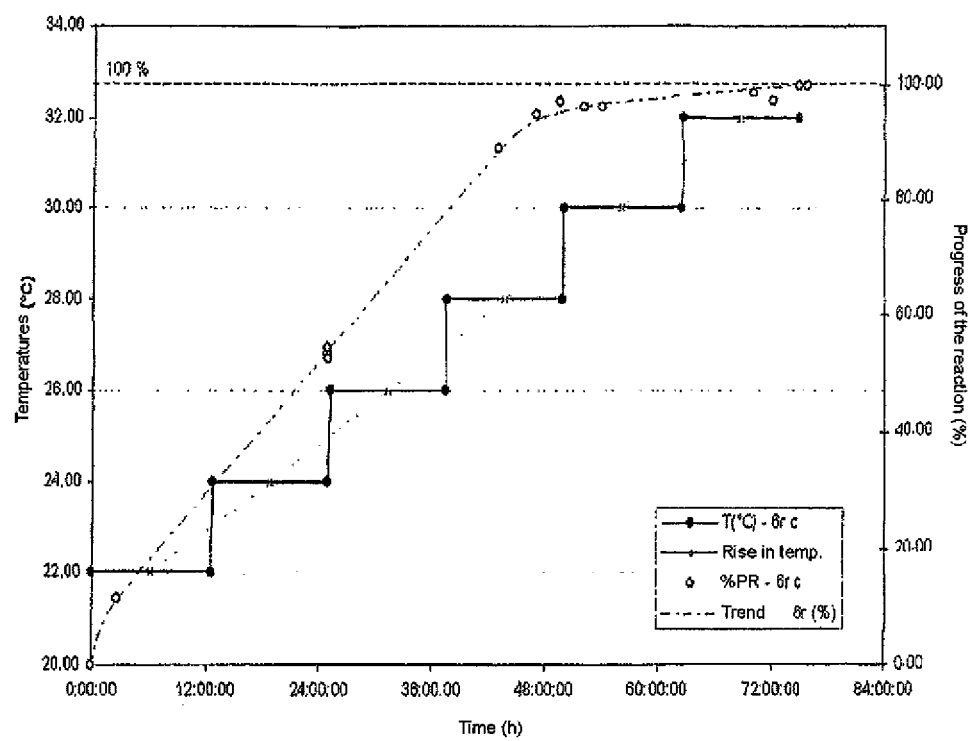
Figure 5:
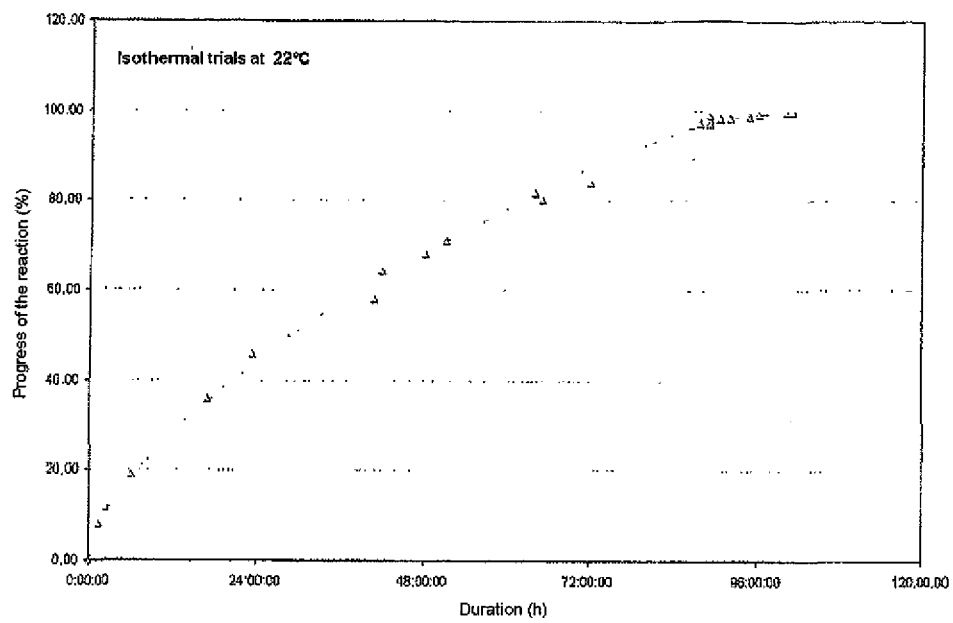
Figure 6:
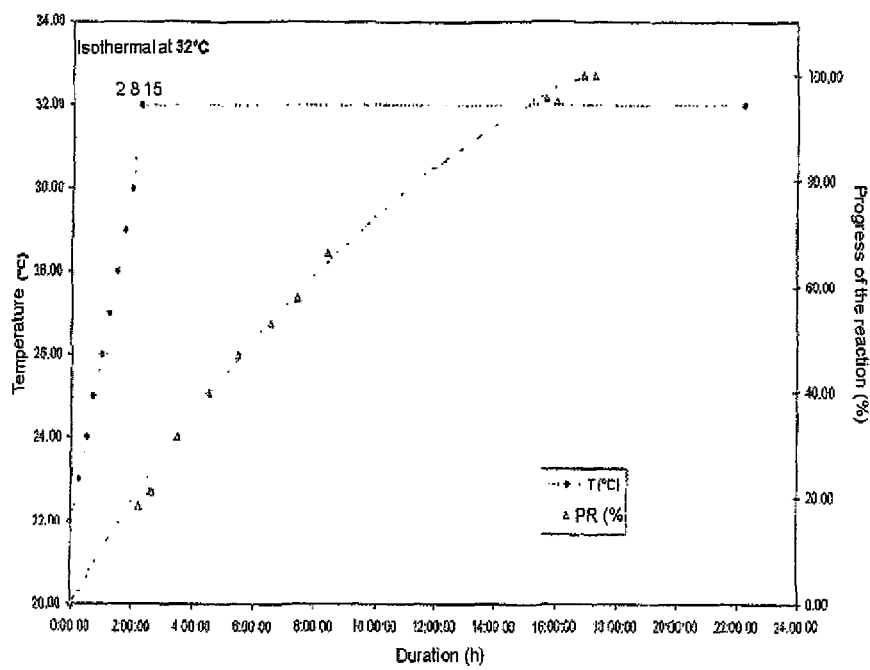

Other characteristics and advantages will emerge from the detailed description of the process for the ammonolysis of 11-bromoundecanoic acid according to the invention which will follow and from the appended figures, in which:

FIG. 1 illustrates an alternative embodiment of the ammonolysis process according to the invention, in which stage ii) takes place continuously in an array of reactors mounted in series R1, R2, . . . Rn, $2 \leq n \leq 25$, each of these reactors being independently maintained at a constant and controlled temperature T1, T2, . . . Tn respectively, FIG. 2 illustrates another alternative embodiment of the ammonolysis process according to the invention, in which stage ii) takes place continuously in an array of reactors mounted in parallel R'1, R'2, . . . R'n, $2 \leq n \leq 25$, each of these reactors being subjected to a variable temperature, FIG. 3 illustrates a third alternative embodiment of the ammonolysis process according to the invention, in which stage ii) takes place noncontinuously (batch mode) in a reactor subjected to a variable temperature Tf, FIG. 4 illustrates the variation in the temperature as a function of the time and also the kinetics of the reaction (variation in the progress of the reaction as a function of the time) in a batch trial according to the invention, with temperature rise in six stationary phases, FIG. 5 illustrates the variation in the temperature as a function of the time and also the kinetics of the reaction (variation in the progress of the reaction as a function of the time) in a comparative batch trial, with the reaction being carried out isothermally at 22° C., FIG. 6 illustrates the variation in the temperature as a function of the time and also the kinetics of the reaction (variation in the progress of the reaction as a function of the time) in a comparative batch trial, with the reaction being carried out isothermally at 32° C.

A subject matter of the present invention is a process for the ammonolysis of 11-bromoundecanoic acid, comprising the following stages:

i) a stage of dispersion of molten or non-molten 11-bromoundecanoic acid in an aqueous ammonia solution, the ammonia being in excess, and ii) a stage of ammonolysis by reaction of 11-bromoundecanoic acid with aqueous ammonia under conditions of stirring the reaction medium and of gradual heating of the latter which are sufficient to make it possible to obtain 11-aminoundecanoic acid with complete consumption of the 11-bromoundecanoic acid in less than 80 h.

The ammonolysis of the 11-bromoundecanoic acid is carried out according to the following sequence of reactions:

formation and dissolution of the ammonium salt of 11-bromoundecanoic acid:

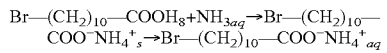

ammonolysis of the ammonium salt of 11-bromoundecanoic acid:

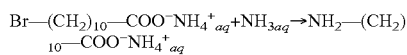

hydrolysis of the ammonium salt of 11-aminoundecanoic acid and precipitation of 11-aminoundecanoic acid:

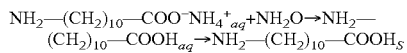

hydroxylation of the ammonium salt of 11-bromoundecanoic acid:

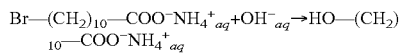

aminolysis of the ammonium salt of 11-aminoundecanoic acid:

Stage i) takes place by dispersion of molten 11-bromoundecanoic acid (hereinafter denoted by the abbreviation Br11), preferably at a temperature of 60° C. to 100° C., in concentrated aqueous ammonia (preferably from 20 to 50% by weight), in excess with respect to the Br11 (e.g., a Br11:$NH_3$ molar ratio of between 1:10 and 1:60, preferably of 1:30), at a temperature ranging from 0° C. to 10° C., via an injection system.

Characteristically, the reaction for the ammonolysis of 11-bromoundecanoic acid takes place under specific temperature conditions, namely with the reaction being carried out at an increasing and non-isothermal temperature. More specifically, the reaction medium is gradually heated (either by virtue of a program of increasing temperatures or by discharging the reaction medium into a sequence of reactors maintained in isolation at temperatures which are fixed but which increase between two consecutive reactors). It is thus possible to accelerate the reaction kinetics and to reduce the reaction time, at complete consumption of the 11-bromoundecanoic acid, in a very significant way, namely to less than 80 h and preferably to less than 75 h.

Advantageously, the process according to the invention makes it possible to reduce the amount of undesired products formed in parallel, in particular the amount of aminodiundecanoic acid, the level of which in the crude reaction product obtained remains below 3500 ppm, preferably below 2500 ppm.

According to a first alternative embodiment, stage ii) advantageously takes place continuously in an array of reactors in series R1, R2, ... Rn, $2 \leq n \leq 25$, independently maintained at a controlled temperature (T1, T2, ... Tn), as shown in the appended FIG. 1. The temperature profile of the array of reactors is characterized by an increasing temperature between consecutive reactors which makes it possible preferably to operate between 15 and 25° C. for the first reactor (that receiving the dispersion of 11-bromoundecanoic acid in aqueous ammonia) and at a preferential temperature of 26 to 40° C. for the final reactor. In this alternative embodiment, the reaction medium is transferred from a given reactor to the consecutive reactor and, the mean residence time in each reactor being from 1 h to 30 h, the total duration of the reaction which makes possible the complete consumption of 11-bromoundecanoic acid is from 20 to 80 h.

The control of the temperature of each reactor is preferably carried out by combining the control of the inlet temperature of the ingredients (11-bromoundecanoic acid and aqueous ammonia) during stage i), the control of the degassing of the excess ammonia in each reactor of stage ii) (endothermic phenomenon which makes it possible to cool the medium) and the use of thermoregulated systems for heating the reactors of stage ii).

According to a second alternative embodiment, stage ii) takes place in an array of reactors in parallel R1, R2, ... Rn, $2 \leq n \leq 25$, independently maintained at a variable temperature, as shown in the appended FIG. 2. Each reactor has a program for a rise in temperature over a given period of time which is dependent on the temperatures chosen. In each reactor, the starting temperature of the program is preferably between 15 and 25° C. and the final temperature from 26 to 40° C. The duration of the reaction, which makes possible the complete consumption of 11-bromoundecanoic acid, varies from 20 h to 80 h according to the starting and final temperatures and the temperature rise program. In order to maintain constant, regular and continuous feeding and withdrawing at the inlet and outlet of the array of reactors, each reactor operates according to loading/reaction/emptying cycles with an offset in time equivalent to the reaction time divided by the number of reactors (n).

According to a third alternative embodiment, stage ii) takes place non-continuously (batch mode) in a reactor maintained at a variable temperature Tf, as illustrated in the appended FIG. 3. This reactor has a program for rise in temperature over a given number of stationary phases or a gradient for rise in temperature over a given period of time which is dependent on the temperatures chosen. The starting temperature of the reactor is preferably between 15 and 25° C. and the final temperature of the reactor from 26 to 40° C. The duration of the reaction, which makes possible the complete consumption of 11-bromoundecanoic acid, varies from 20 h to 80 h according to the starting and final temperatures and the temperature rise program.

For each of the alternative embodiments of the ammonolysis process, a distinction should be made between the residence time and the reaction time: the residence time depends on the configuration of the plant, characterized, for example, by the volume and the number of reactors, the direction of flow, the stirring or the flow rates, whereas the reaction time depends only on the parameters capable of influencing the reaction kinetics, including the temperatures and the concentrations.

In its third alternative form, the ammonolysis process according to the invention also comprises a stage iii) of filtration, washing and pulling dry, carried out on the 11-aminoundecanoic acid obtained at the end of stage ii). The reaction product thus obtained is subjected to an additional stage iv) of purification, preferably carried out by the following sequence of operations: redissolution, filtration, crystallization, filtration, washing and pulling dry.

According to a preferred embodiment, the process according to the invention also comprises a stage v) of recovery of the residual 11-aminoundecanoic acid in the various filtrates and wash liquors obtained in stages iii) and/or iv), by degassing of the ammonia, liquid/liquid extraction, crystallization, filtration and washing.

The ammonolysis process according to the invention additionally comprises a final stage of drying the 11-aminoundecanoic acid obtained in stage iv), optionally with the addition of that obtained in stage v).

The 11-aminoundecanoic acid thus obtained contains a moderate amount of impurities, mainly aminodiundecanoic acid. Its use as monomer in a condensation reaction makes it possible to obtain a polyamide PA11 or Rilsan® of very good quality.

A better understanding of the invention will be obtained on reading the following implementational examples which do not limit the invention.

EXAMPLE 1 ACCORDING TO THE INVENTION

Batch Trial with Rise in Temperature in 6 Stationary Phases 660 g of 32% aqueous ammonia are placed at 0° C. in a jacketed one-liter reactor equipped with a stirrer shaft provided with two 5-bladed propellers rotating at a speed of 400 rpm. 110 g of molten 11-bromoundecanoic acid are added at 90° C. by rapid dropwise addition. The reaction takes place at atmospheric pressure. On completion of the addition of the brominated acid, the set point for the temperature of the medium is increased to 22° C. and then a rise in temperature from 22° C. to 32° C. is imposed on the reaction medium while observing 6 stationary phases of 12 h 30 at 22° C., 24° C., 26° C., 28° C., 30° C. and 32° C.

The progress of the reaction (% PR) is defined as being the level of 11-bromoundecanoic acid consumed as a function of the starting amount of acid. The amount of brominated acid consumed is determined by quantitative determination, by potentiometry (titration with a silver electrode and by silver nitrate), of the bromine ions released by the reaction into the medium. The temperature profile (temperature as a function of the time) and the kinetics of the reaction (% PR as a function of the time) are presented in FIG. 4.

The final crude reaction product is recovered in this state in the form of a free-flowing suspension and is then degassed by heating. The quantitative determination of the aminodiundecanoic acid in this crude product is carried out by HPLC.

COMPARATIVE EXAMPLE 2

Isothermal Batch Trial at 22° C.

660 g of 32% aqueous ammonia are placed at 0° C. in a jacketed one-liter reactor equipped with a stirrer shaft provided with two 5-bladed propellers rotating at a speed of 400 rpm. 110 g of molten 11-bromoundecanoic acid are added at 90° C. by rapid dropwise addition. The reaction takes place at atmospheric pressure. On completion of the addition of the brominated acid, the set point for the temperature of the medium is increased to 22° C. and is then maintained at 22° C. until the 11-bromoundecanoic acid has been completely consumed.

The temperature profile (temperature as a function of the time) and the kinetics of the reaction (% PR as a function of the time) are presented in FIG. 5.

The final crude reaction product is recovered in this state in the form of a free-flowing suspension and is then degassed by heating. The quantitative determination of the aminodiundecanoic acid in this crude product is carried out by HPLC.

COMPARATIVE EXAMPLE 3

Isothermal Batch Trial at 32° C.

660 g of 32% aqueous ammonia are placed at 0° C. in a jacketed one-liter reactor equipped with a stirrer shaft provided with two 5-bladed propellers rotating at a speed of 400 rpm. 110 g of molten 11-bromoundecanoic acid are added at 90° C. by rapid dropwise addition. The reaction takes place at atmospheric pressure. On completion of the addition of the brominated acid, the set point for the temperature of the medium is gradually increased to 32° C. and is then maintained at 32° C. until the brominated acid has been completely consumed.

The temperature profile (temperature as a function of the time) and the kinetics of the reaction (% PR as a function of the time) are presented in FIG. 6.

The final crude reaction product is recovered in this state in the form of a free-flowing suspension and is then degassed by heating. The quantitative determination of the aminodiundecanoic acid in this crude product is carried out by HPLC.

These results are presented in the following table I.

TABLE I

|  | Example 1 6 stationary phases | Example 2 iso 22° C. | Example 3 iso 32° C. |
| --- | --- | --- | --- |
| time (min) to achieve 100% consumption of Brl 1 | 4490 | 6060 | 1370 |
| A2 (mg/kg) | 2310 | 2051 | 3848 |

A2 represents the level of aminodiundecanoic acid in the final crude reaction product, expressed in ppm or mg of aminodiundecanoic acid per kg of suspension.

Comparative examples 2 and 3 correspond to two cases for which the ammonolysis reaction takes place at a constant temperature until the 11-bromoundecanoic acid has been completely consumed. It is thus necessary to maintain the reaction medium at 22° C. for 6060 min in order to completely consume the 11-bromoundecanoic acid (example 2). According to example 3, the reaction time can be greatly reduced (−77.4%) by maintaining the medium at a higher temperature (32° C.) but the amount of aminodiundecanoic acid formed is found to be very greatly increased thereby (+87.6%).

Example 1 according to the invention corresponds to an ammonolysis reaction carried out at a temperature which increases according to 6 stationary temperature phases from 22° C. to 32° C. A comparison with example 2 shows that it is possible to reduce the reaction time (by −25.9%) while conceding only a slight increase in aminodiundecanoic acid of the order of 12.6%.

What is claim is:

1. A process for the manufacture of 11-aminoundecanoic acid from 11-bromoundecanoic acid, comprising the following stages:
   i) dispersing molten or non-molten 11-bromoundecanoic acid in an aqueous ammonia solution, and
   ii) reacting 11-bromo-undecanoic acid with excess aqueous ammonia under conditions of stirring the reaction medium and of gradual heating of the latter in an ammonolysis step to form 11 aminoundecanoic acid.

2. The process as claimed in claim 1, in which stage ii) takes place continuously in an array of reactors in series R1, R2, ... Rn, 2 ≦ n ≦ 25, R1 being the reactor which receives the dispersion of 11-bromoundecanoie acid in aqueous ammonia, each of these reactors being independently maintained at a constant and controlled temperature T1, T2, ... Tn respectively, the temperature of the array of reactors increasing between two consecutive reactors.

3. The process as claimed in claim 2, in which the temperature T1 of the reactor R1 is from 15 to 25° C. and the temperature Tn of the final reactor Rn is from 26 to 40° C.

4. The process as claimed in claim 2, in which the control of the temperature of each reactor is carried out by combining the control of the inlet temperature of the ingredients (11-bromoundecanoic acid and aqueous ammonia) during stage i), the control of the degassing of the excess ammonia in each reactor of stage ii) and the use of thermoregulated systems for heating the reactors R1 to Rn.

5. The process as claimed claim 2, in which, the reaction medium being transferred from a given reactor to the consecutive reactor and the mean residence time in each reactor being from 1 hour to 30 hours, the total duration of the reaction which makes possible the complete consumption of 11-bromoundecanoic acid is from 20 to 80 hours.

6. The process as claimed in claim 1, in which stage ii) takes place in an array of reactors in parallel R'1, R'2, ... R'n, 2 ≦ n ≦ 25, each of these reactors being subjected to a variable temperature.

7. The process as claimed in claim 6, in which the starting temperature of each reactor is from 15 to 25° C. and the final temperature of each reactor is from 26 to 40° C.

8. The process as claimed in claim 6, in which each reactor operates according to loading/reaction/emptying cycles with an offset in time equivalent to the reaction time divided by the number of reactors n, in order to maintain constant, regular and continuous feeding and withdrawing at the inlet and outlet of the array of reactors.

9. The process as claimed in claim 1, in which stage ii) takes place non-continuously in a reactor subjected to a variable temperature Tf, said reactor having a program for rise in temperature over a given number of stationary phases or a gradient for rise in temperature, the duration of which depends on the temperature chosen.

10. The process as claimed in claim 9, in which the starting temperature of the reactor is from 15 to 25° C. and the final temperature of the reactor is from 26 to 40° C.

11. The process as claimed in claim 6, in which the duration of the reaction, which makes possible the complete consumption of 11-bromoundecanoic acid, varies from 20 hours to 80 hours according to the starting and final temperatures and the temperature rise program.

12. The process as claimed in claim 9, in which a rise in temperature from 22° C. to 32° C. is imposed on the reaction medium while observing 6 stationary phases of 12 hours 30 min at 22° C., 24° C., 26° C., 28° C., 30° C. and 32° C.

13. The process as claimed in claim 1, additionally comprising a stage iii) of filtering, washing and pulling dry, carried out on the 11-aminoundecanoic acid obtained at the end of stage ii).

14. The process as claimed in claim 13, additionally comprising a stage iv) of purifying the 11-aminoundecanoic acid obtained at the end of stage iii).

15. The process as claimed in claim 14, additionally comprising a stage v) of recovering the residual 11-aminoundecanoic acid in the various filtrates and wash liquors obtained in stages iii) and/or iv), by degassing of the ammonia, liquid/liquid extraction, crystallization, filtration and washing.

16. The process as claimed in claim 14, additionally comprising a final stage of drying the 11-aminoundecanoic acid obtained in stage iv), optionally with the addition of that obtained in stage v).

17. The process as claimed in claim 1, in which the level of aminodiundecanoic acid in the crude reaction product obtained is less than 3500 ppm, preferably less than 2500 ppm.

18. The process as claimed in claim 1, in which the duration of the ammonolysis stage resulting in the complete consumption of 11-bromoundecanoic acid is less than 75 hours.

19. The process as claimed in claim 14, wherein stage iv) of purifying the 11-atninoundecanoic acid obtained at the end of stage iii) occurs using the following sequence of operations: redissolution, filtration, crystallization, filtration, washing and pulling dry.

20. The process as claimed in claim 17, in which the level of aminodiundecanoic acid in the crude reaction product obtained is less than 2500 ppm.

* * * * *